United States Patent
Kuhn et al.

(10) Patent No.: US 7,183,444 B2
(45) Date of Patent: Feb. 27, 2007

(54) METHOD FOR PRODUCING ANIS ALCOHOL

(75) Inventors: Walter Kuhn, Holzminden (DE);
Hans-Ulrich Funk, Lauenforde (DE);
Gerhard Senft, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 0 days.

(21) Appl. No.: 10/512,069

(22) PCT Filed: Apr. 9, 2003

(86) PCT No.: PCT/EP03/03647

§ 371 (c)(1),
(2), (4) Date: Dec. 7, 2005

(87) PCT Pub. No.: WO03/089395

PCT Pub. Date: Oct. 30, 2003

(65) Prior Publication Data

US 2006/0088559 A1    Apr. 27, 2006

(30) Foreign Application Priority Data

Apr. 22, 2002 (DE) .............................. 102 17 798

(51) Int. Cl.
*C07C 41/18* (2006.01)

(52) U.S. Cl. ............................................ 568/648

(58) Field of Classification Search ................ 568/648
See application file for complete search history.

(56) References Cited

U.S. PATENT DOCUMENTS 2,046,011 A * 6/1936 Amend ........................ 549/445
3,663,626 A * 5/1972 Arrigo et al. ................ 568/650
5,800,897 A * 9/1998 Sharma et al. ................ 428/74

FOREIGN PATENT DOCUMENTS

JP    08238098    9/1996

OTHER PUBLICATIONS

Dewey, Robert Levering, et al, "The Promoter Effect of Platinic Chloride on Raney Nickel. I. General Effects on Type W-6 Catalyst", J. Am. Chem. Soc., Bd. 72, 1950, vol. 72, pp. 1190-1194; XP-002250853.

Nishimura, Takahiro et al, "Palladium(II)-Catalyzed Oxidation of Alcohols to Aldehydes and Ketones by Molecular Oxygen", J. Org. Chem., Bd. 64, 1999, pp. 6750-6755; XP-002250854.

* cited by examiner

*Primary Examiner*—Rosalynd Keys
(74) *Attorney, Agent, or Firm*—Roylance, Abrams, Berdo & Goodman, L.L.P.

(57) ABSTRACT

The present invention relates to a method for the preparation of anisalcohol (methoxybenzyl alcohol) by hydrogenation of anisaldehyde (methoxybenzaldehyde) in the presence of Raney nickel and a basic additive, the use of the anisalcohol and hygiene or care products containing anisalcohol.

8 Claims, No Drawings

METHOD FOR PRODUCING ANIS ALCOHOL

The present invention relates to a method for the preparation of anisalcohol (methoxybenzyl alcohol) by hydrogenation of anisaldehyde (methoxybenzaldehyde) in the presence of Raney nickel and a basic additive, the use of the anisalcohol and agents containing anisalcohol.

p-Anisalcohol (4-methoxybenzyl alcohol) is an important and widely used fragrance with a sweet-flowery, slight balsamic odour. Anisalcohol occurs, for example, in vanilla pods and anise seeds. (K. Bauer, A. Garbe, Common Fragrance and Flavor Materials, p. 89, VCH, Weinheim, 1985.; S. Arctander, Perfume and Flavour Chemicals, No. 249 1969).

The hydrogenation of anisaldehyde to anisalcohol using Raney nickel with the addition of platinum(IV) chloride and triethylamine is described in J. Am. Chem. Soc. 1959, 72, 1190. The hydrogenation is carried out in ethanol as solvent and gives anisalcohol in 86% yield.

The electrocatalytic hydrogenation of anisaldehyde to anisalcohol using Raney nickel is described in Bull. Chem. Soc. Jp. EN 3, 1983, 56, 719. The nickel cathode is coated with Raney nickel powder and in methanolic solution at room temperature leads to anisalcohol in 71% yield.

The known methods are, on the one hand, not satisfactory because of the expensive catalysts, some of which are also laborious to prepare; on the other hand, the yields are inadequate.

The aim was to find a method for the preparation of anisalcohol that is able to yield the anisalcohol in better yield and in high purity.

The present invention therefore relates to a method for the preparation of anisalcohol by hydrogenation of anisaldehyde, characterised in that the hydrogenation is carried out in the presence of Raney nickel and a basic additive selected from the series comprising metal hydroxides or metal alcoholates.

A further subject of the present invention is the use of the anisalcohol prepared according to the invention as a fragrance and also agents containing this anisalcohol.

The method according to the invention enables, in particular, the preparation of anisalcohol that is flawless from the sensory standpoint, in particular under economic aspects and on the industrial scale.

Raney nickel catalysts are known per se (Methoden der organischen Chemie (Methods of Organic Chemistry)/Houben Weyl, Volume IV/lc, Reduktion Teil 1 (Reduction Part 1), Georg Thieme Verlag, Stuttgart, 1980, pages 15 to 562).

The hydrogenation of epoxides in the presence of Raney nickel and a basic substance is described in WO-A 2000/26165.

o-Anisaldehyde, p-anisaldehyde, m-anisaldehyde or an arbitrary mixture of the said aldehydes can be used for the method according to the invention. p-Anisaldehyde is preferably employed in the hydrogenation.

For the method according to the invention the Raney nickel can be used in the dry or moist state (water content up to 70% (m/m)).

For the method according to the invention the weight ratio of the Raney nickel employed to anisaldehyde is 0.0001 to 0.1 to 1, preferably 0.001 to 0.05 to 1, particularly preferentially 0.01 to 0.02 to 1.

For the method according to the invention the basic additive can be a metal hydroxide or a metal alcoholate. Alkali metal hydroxides and alkaline earth metal hydroxides and also alkali metal alcoholates and alkaline earth metal alcoholates are preferred, the alcoholates preferably having no more than 4 carbon atoms. Particularly preferred basic additives are sodium hydroxide, potassium hydroxide, sodium methylate and sodium ethylate.

The basic additives can be employed in the pure form or in the form of solutions. Aqueous solutions are particularly suitable in the case of the hydroxides and alcoholic solutions are particularly suitable in the case of the alcoholates.

Particularly preferred solutions containing basic additives are aqueous sodium hydroxide solution and methanolic sodium methylate solution.

For the method according to the invention the weight ratio of the basic additive employed, based on the pure form thereof, to anisaldehyde is 0.000001 to 0.1 to 1, preferably 0.00001 to 0.01 to 1, particularly preferentially 0.0001 to 0.001 to 1.

According to the invention the method is carried out at 30–180° C., preferably at 70–130° C., and particularly preferentially at 80–100° C.

The method according to the invention is carried out with hydrogen; the hydrogen pressures are usually in the range of 1 to 100 bar abs.; it is preferred to carry out the reaction under hydrogen pressures in the range of 5 to 50 bar abs., in particular in the range of 10 to 20 bar abs.

The reaction time is usually in the range of 2 to 100 hours, preferably in the range of 5 to 40 hours and particularly preferentially in the range of 20 to 25 hours.

The method can be carried out continuously, semi-continuously and discontinuously.

The method according to the invention can be carried out using solvents or solvent mixtures. For example, alcohols, aqueous alcohols, ethers, esters, aromatic or saturated hydrocarbons are suitable. Usually solvents such as methanol, ethanol, isopropanol, n-propanol, isobutanol, n-butanol, sec-butanol, tetrahydrofuran, dibutyl ether, ethylene glycol dimethyl ether, ethyl acetate, methyl acetate, pentane, hexane, heptane, octane, cyclopentane, cyclohexane, methylcyclohexane, cyclooctane, benzene, toluene, ethylbenzene and xylenes can be used.

The method is preferably carried out solvent-free.

The method according to the invention can, for example, be carried out as follows:

Anisaldehyde, Raney nickel and basic additive are initially introduced into a pressure vessel. The hydrogenation is carried out at the selected temperature and under the selected hydrogen pressure. After the end of the hydrogenation, the crude anisalcohol can be obtained by removal of the Raney nickel (for example by filtration, decanting or centrifuging) and, if appropriate, by removal of the basic additive via washing operations. If required, a further purification of the anisalcohol can be carried out, for example by distillation.

According to the method according to the invention, anisalcohol can be obtained in a purity of more than 99% and a distilled yield of 99%.

The anisalcohol prepared by the method according to the invention can be used without further purification steps; in particular, it is of good quality from the perfume standpoint.

The anisalcohol prepared by the method according to the invention can be used in particular as a fragrance, in fragrance mixtures, perfume compositions, perfume oils or scent compositions.

Hygiene or care products, in particular in the field of household products and personal hygiene products, are a further field of use.

The perfume oils containing anisalcohol prepared by the method according to the invention can be used in concentrated form, in solutions or in some other modified form for the preparation of, for example, perfume extracts, eau de parfums, eau de toilettes, aftershaves, eau de colognes, pre-shave products, splash colognes and perfumed freshening wipes and for perfuming acid, alkaline and neutral cleaning agents, such as, for example, floor cleaners, window cleaners, washing-up liquids, bath and sanitary equipment cleaners, scouring agents, solid and liquid WC cleaners, carpet cleaners in powder and foam form, liquid detergents, powder detergents, laundry pre-treatment agents, such as bleaching agents, softeners and stain removers, fabric conditioners, laundry soaps, laundry tablets, disinfectants, surface disinfectants and air fresheners in liquid or gel form or applied to a solid support, aerosol sprays, waxes and polishes, such as furniture polishes, floor waxes, cream shoe polishes and personal hygiene agents, such as, for example, solid and liquid soaps, shower gels, shampoos, shaving soaps, shaving foams, bath oils, cosmetic emulsions of the oil-in-water, of the water-in-oil and of the water-in-oil-in-water type, such as, for example, skin creams and lotions, face creams and lotions, sun protection creams and lotions, after-sun creams and lotions, hand creams and lotions, foot creams and lotions, depilatory creams and lotions, aftershave creams and lotions, bronzing creams and lotions, hair care products, such as, for example, hair sprays, hair gels, hair lotions, hair rinses, permanent and semi-permanent hair dyes, hair shaping agents such as cold permanent waves, and hair smoothing agents, hair tonics, hair creams and lotions, deodorants and antiperspirants, such as, for example, underarm sprays, roll-ons, deodorant sticks, deodorant creams or make-up products.

The following example illustrates the invention.

EXAMPLE

Into a stirred autoclave with gasifying stirrer was introduced 3000 g anisaldehyde (GC purity 99.7%.), 7.5 g 21% sodium methylate solution in methanol and 57 g moist Raney nickel (50% water content). The hydrogenation was carried out for 21 hours at 80 to 100 ° C and 13 bar. After filtration, 3015 g anisalcohol with a purity of 99.1% were obtained. It was possible to distill the anisalcohol obtained at 130 °C sump temperature and 1 m bar vacuum. The theoretical yield was 99%

The invention claimed is:

1. A method for the preparation of anisalcohol by hydrogenation of anisaldehyde, wherein said hydrogenation is carried out in the presence of Raney nickel and a basic additive comprising a metal hydroxide or metal alcoholate.

2. A method according to claim 1, characterised in that the basic additive comprises sodium hydroxide, potassium hydroxide, sodium methylate or sodium ethylate.

3. The method of claim 1, wherein the basic additive is an alkali metal hydroxide or alkali metal alcoholate.

4. The method of claim 1, wherein the basic additive is an aqueous alkali metal hydroxide solution.

5. The method of claim 1, wherein the basic additive is an alcoholic solution of sodium methylate or sodium ethylate.

6. The method of claim 1, wherein said basic additive is included in an amount of, based on the pure form thereof, 0.000001–0.1 to 1 based on the weight of the anisaldehyde.

7. The method of claim 6, wherein said Raney nickel is included in an amount of 0.0001–0.1 to 1 based on the weight of the anisaldehyde.

8. The method of claim 1, wherein the basic additive is an alkaline earth metal hydroxide.

* * * * *